(12) United States Patent
Shalaby et al.

(10) Patent No.: US 7,041,308 B2
(45) Date of Patent: May 9, 2006

(54) DRUG-POLYMER COATED STENTS WITH SEGMENTED HOMOCHAIN COPOLYESTERS

(75) Inventors: Shalaby W. Shalaby, Anderson, SC (US); Todd Campbell, Petaluma, CA (US)

(73) Assignee: Poly-Med, Inc., Anderson, SC (US)

( * ) Notice: Subject to any disclaimer, the term of this patent is extended or adjusted under 35 U.S.C. 154(b) by 190 days.

(21) Appl. No.: 10/393,880

(22) Filed: Mar. 20, 2003

(65) Prior Publication Data

US 2003/0199964 A1 Oct. 23, 2003

Related U.S. Application Data

(60) Provisional application No. 60/374,268, filed on Apr. 18, 2002.

(51) Int. Cl.
*A61F 2/00* (2006.01)
*A61F 2/06* (2006.01)
*A61K 9/22* (2006.01)

(52) U.S. Cl. .................. 424/425; 623/1.11; 604/891.1
(58) Field of Classification Search ...................... 424/1
See application file for complete search history.

(56) References Cited

U.S. PATENT DOCUMENTS 6,228,845 B1 * 5/2001 Donovan et al. ............. 514/44
6,344,035 B1 * 2/2002 Chudzik et al. ............ 604/265

FOREIGN PATENT DOCUMENTS

WO WO 0059963 A1 10/2000
WO WO 02087586 A1 11/2002

OTHER PUBLICATIONS

Lowe et al.; Well-defined sulfobetaine-based statistical copolymers as potential antibioadherent coatings; Journal of Biomedical Materials Research, Oct. 2000, vol. 52, No. 1, pp. 88-94.

* cited by examiner

*Primary Examiner*—Thurman K. Page
*Assistant Examiner*—Casey Hagopian

(57) ABSTRACT

The present invention provides a system for treating a vascular condition, including a catheter, a stent coupled to the catheter, a polymeric coating on the stent including a segmented homochain copolyester, and a bioactive drug dispersed within the polymeric coating.

24 Claims, 4 Drawing Sheets

DRUG-POLYMER COATED STENTS WITH SEGMENTED HOMOCHAIN COPOLYESTERS

This application claims priority to U.S. Provisional Patent Application Ser. No. 60/374,268, filed Apr. 18, 2002.

FIELD OF THE INVENTION

This invention relates generally to biomedical stents. More specifically, the invention relates to a segmented homochain copolyester coating with a dispersed bioactive agent on an endovascular stent for in vivo, timed-release drug delivery.

BACKGROUND OF THE INVENTION

Copolymerization is a well-established strategy to produce new materials from one or more monomers, with tailored properties for specific applications. Copolymerization is commonly used to prepare homochain copolymers with carbon-carbon main chains, and heterochain copolymers with carbon and other types of atoms in the polymer backbone or main chain. The sequence distribution of these copolymers can be random and non-random. For heterochain copolymers, the non-random chains may comprise block copolymers, i.e. blocks with a high number of covalently bonded repeat units of the same chemical composition; segment copolymers, i.e. segments with a small number of repeat units; or graft copolymers, i.e. side-chain grafts with a variable number of repeat units of at least one of the constituents. For homochain polymers, the non-random parts of the chains commonly comprise block and graft copolymers. These copolymers were developed over forty years ago as the A-B-A and A-B types of homochain block copolymers comprising polydiene and polystyrene long sequences as the A and B blocks, respectively. The polydiene and polystyrene block copolymers having no functional pendant group have been commercialized as thermoplastic elastomers with the combined properties of elastomers that exhibit elasticity at room temperature, and thermoplastics with their melt processability attributes. The unique properties of these copolymers have been covered in a number of reviews, such as S. W. Shalaby and H. E. Bair, Chapter 4 in *Thermal Characterization of Block Copolymers and Polyblends*, E. A. Turi, Ed., Academic Press, 1981. However, nothing in the prior art has been disclosed on tailoring the structure of a homochain, linear segmented or random copolyester with segmented grafts having repeat units with pendant ester groups (e.g., those derived from vinyl acetate and alkyl methacrylates) to impart certain properties for a sought biomedical application. These structures, with or without the segmented grafts, are herein referred to as segmented homochain copolyesters. Exploration of homochain polyesters has been extended to studying the formation of linear segmented homochain copolyesters and random copolymers with segmented grafts and unique properties for use as an effective metal-adhering barrier coating, with or without a bioactive agent, for blood-contacting biomedical implanted devices.

The efficacy of endovascular stents may be increased by the addition of stent coatings that contain pharmaceutical drugs. These drugs may be released from the coating while in the body, delivering their patent effects at the site where they are needed. The localized levels of the medications may be high, and therefore potentially more effective than orally or intravenously delivered drugs that distribute throughout the body, and which may have little effect on the impacted area, or may be expelled rapidly from the body without reaching their pharmaceutical intent. Furthermore, drug release from tailored stent coatings may have controlled, timed-release qualities, eluting their bioactive agents over hours, weeks or even months.

A composition with a bioactive agent for coating the surface of a medical device based on poly (alkyl)(meth)acrylate and poly(ethylene-co-vinyl acetate) is described in "Bioactive Agent Release Coating," Chudzik, et al., U.S. Pat. No. 6,214,901, issued Apr. 10, 2001. A composite polymer coating with a bioactive agent and a barrier coating formed in situ by a low energy plasma polymerization of a monomer gas is described in "Polymeric Coatings with Controlled Delivery of Active Agents," K. R. Kamath, publication WO 00/32255, published 8 Jun. 2000. A polymeric coating for an implantable medical article based on hydrophobic methacrylate and acrylate monomers, a functional monomer having pendant chemically reactive amino groups capable of forming covalent bonds with biologically active compounds, and a hydrophilic monomer wherein a biomolecule is coupled to the coated surface, is presented in "Implantable Medical Device," E. Koulik, et al., U.S. Pat. No. 6,270,788, issued Aug. 7, 2001. Use of block copolymers on a hydrophobic polymer substrate is described in "Biocompatible Polymer Articles," E. Ruckenstein, et al., U.S. Pat. No. 4,929,510, issued May 29, 1990. A method for the columetic inclusion and grafting of hydrophilic compounds in a hydrophobic substrate using an irradiation means is described in "Hydrophobic Substrate with Grafted Hydrophilic Inclusions," G. Gaussens, et al., U.S. Pat. No. 4,196,065, issued Apr. 1, 1980.

Unfortunately, drug polymers may not provide the mechanical flexibility necessary to be effectively used on a stent. The stent may be deployed by self-expansion or balloon expansion, accompanied by a high level of bending at portions of the stent framework, causing cracking, flaking, peeling, or delaminating of many candidate drug polymers while the stent diameter is increased by threefold or more during expansion. The candidate drug polymer may not stick or adhere, or may elute its pharmacologically active constituents too quickly or too slowly, or possibly in a toxic manner. One drug may elute much faster than a second drug in the same drug polymer, making the controlled delivery of a single drug or multiple drugs difficult. If a drug is eluted too quickly, it may be ineffective and possibly toxic. If a drug is eluted too slowly, then its intended effect on the body may be compromised. Furthermore, the coating may fall off, crystallize or melt during preparation and sterilization prior to deployment, further limiting the types of drug polymers acceptable for use on cardiovascular stents.

A drug-polymer system that can be tailored to the desired elution rate for a specific drug may be beneficial. It is desirable to have a drug-polymer system that can be tailored to accommodate a variety of drugs for controlled time delivery, while maintaining mechanical integrity during stent deployment. A polymeric system that can be readily altered to control the elution rate of an interdispersed bioactive drug and to control its bioavailability may be of further benefit.

It is an object of this invention, therefore, to provide a system for treating heart disease and other vascular conditions, to provide methods of manufacturing drug polymer coated stents, and to overcome the deficiencies and limitations described above.

SUMMARY OF THE INVENTION

One aspect of the invention provides a system for treating a vascular condition, including a catheter, a stent coupled to the catheter, a polymeric coating on the stent where the polymeric coating includes a segmented homochain copolyester, and a bioactive drug dispersed within the polymeric coating. The segmented homochain copolyester may include a plurality of butyl methacrylate sequences randomly linked to a plurality of vinyl acetate sequences.

The segmented homochain copolyester may include a plurality of segments of a first segment type linked to a single or a plurality of segments of a second segment type, where the second segment type provides a metal-adhering characteristic and the first segment type provides a hydrophobic barrier membrane characteristic. The segmented homochain copolyester may include between five and ninety-five percent by weight of the first segment type. The second segment type may include vinyl acetate and the first segment type may include n-butyl methacrylate. The second segment type may include vinyl acetate and the first segment type comprises t-butyl methacrylate. The second segment type may include ethoxyethyl methacrylate and the first segment type may include n-butyl methacrylate. The second segment type may include ethyl methacrylate and the first segment type comprises n-butyl methacrylate. The second segment type may include methacrylic acid and the first segment type may include n-butyl methacrylate.

A plurality of segmented grafts may be attached to the segmented homochain copolyester. Each of the segmented grafts may include at least one n-butyl methacrylate segment. Each of the segmented grafts may include at least one vinyl acetate segment and at least one n-butyl methacrylate segment.

All types of segmented homochain copolyesters (linear and graft type) described herein comprising vinyl acetate-derived sequences may have said sequences partially or fully hydrolyzed to produce the respective vinyl alcohol based sequences. The latter are created to increase overall hydrophilicity of the copolyester and its propensity for hydrophilic bioactive agents.

The segmented homochain copolyester may be based on a predetermined elution rate of the bioactive drug. The polymeric coating may include between five and seventy-five percent by weight of the bioactive drug.

The bioactive drug may include an antisense agent, an antineoplastic agent, an antiproliferative agent, an antithrombogenic agent, an anticoagulant, an antiplatelet agent, an antibiotic, or an anti-inflammatory agent. The bioactive drug may include a gene therapy agent, a therapeutic substance, an organic drug, a pharmaceutical compound, a recombinant DNA product or a recombinant RNA product. The bioactive drug may include a collagen, a collagenic derivative, a protein, a protein analog, a saccharide, or a saccharide derivative. The bioactive agent may control cellular profileration.

The polymeric coating on the stent may include a primary coat and a cap coat on the primary coat. The primary coat may include a bioactive agent between one and seventy percent by weight interdispersed within the primary coat. The cap coat may include a hydrophobic characteristic. The primary coat may include a vinyl acetate derivative, and the cap coat may include an n-butyl methacrylate derivative. The cap coat may include a second bioactive agent between 0.01 percent and thirty percent by weight interdispersed within the cap coat.

The polymeric coating on the stent may include a fracture strain characteristic of greater than two hundred percent.

The catheter may include a balloon used to expand the stent. The catheter may include a sheath that retracts to allow expansion of the stent. The stent may include a base metal such as stainless steel, nitinol, tantalum, MP35N alloy, a suitable biocompatible alloy, or a suitable biocompatible material.

Another aspect of the invention is a method of manufacturing a drug-polymer stent including the steps of mixing a first monomer and a second monomer in a solution, reacting the mixture to at least twenty percent conversion, polymerizing the mixture by adding an aliquot of one of the second monomer or a mixture of the second monomer and the first monomer, mixing a bioactive agent with the polymerized mixture to form a drug polymer with a predefined elution rate, and coating a stent with the drug polymer.

The solution may include isopropyl alcohol. An incremental amount of free radical may be added to the solution. The polymerization step may include multiple stages of polymerization.

Another aspect of the invention is a method of manufacturing a drug-polymer stent including the steps of dissolving a segmented homochain copolyester with a first liquid in a first solution, mixing a first bioactive agent in the first solution, applying the first solution on a stent to form a primary coat, and drying the primary coat where the primary coat comprises between 1 percent and 70 percent by weight of the first bioactive agent. A segmented homochain copolyester may be dissolved with a second liquid in a second solution. The second solution may be applied to the stent and dried to form a cap coat. The first liquid and the second liquid may be immiscible. The first bioactive agent may be non-soluble in the second liquid.

The method may further include mixing a second bioactive agent in the second solution, wherein the cap coat comprises between 0.01 percent and thirty percent by weight of the second bioactive agent.

Another aspect of the invention is a drug-polymer coated stent, including a stent with a stent framework, and a polymeric coating on the stent framework where the polymeric coating includes a segmented homochain copolyester with an interdispersed bioactive agent.

The aforementioned, and other features and advantages of the invention will become further apparent from the following detailed description of the presently preferred embodiments, read in conjunction with the accompanying drawings. The detailed description and drawings are merely illustrative of the invention rather than limiting, the scope of the invention being defined by the appended claims and equivalents thereof.

DETAILED DESCRIPTION OF THE
PRESENTLY PREFERRED EMBODIMENTS

The present invention provides polymeric formulations of linear segmented homochain copolyesters and graft copolymers with tailored, unique properties for use as a metal-adhering barrier coating for blood-contacting biomedical implants such as stents, and methods of manufacturing these formulations and devices. The segmented homochain copolyester may include segmented grafts attached to the polymer backbone with similar hydrophobic and hydrophilic characteristics as the main chain. The main chain and grafts may include segments with pendant ester groups in each repeat unit to form a segmented homochain copolyester. Metal-adhering attributes may aid in the cohesiveness of the copolymer to metallic stents, whereas hydrophobic attributes may assist in the timed-release control of pharmaceutical compounds interdispersed within the polymeric coating. The formulations may be selected to provide desired elution rates of the embedded bioactive agents.

Figure 1:
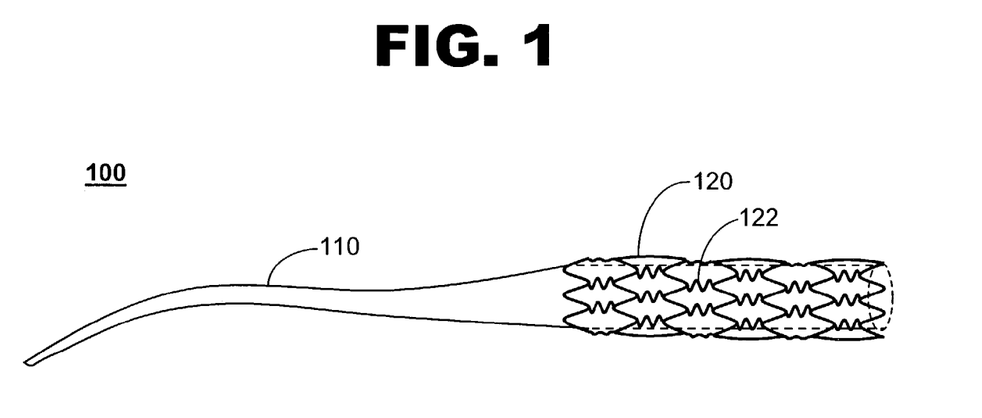
FIG. 1 is an illustration of one embodiment of a system for treating a vascular condition containing a catheter, a stent, and a drug polymer coating the stent, in accordance with the current invention.

One aspect of the present invention is a system for treating heart disease, various cardiovascular ailments, and other vascular conditions using catheter-deployed endovascular stents with tailored polymeric coatings for controlling the timed-release properties of interdispersed bioactive agents. Treatment of vascular conditions may include the prevention or correction of various ailments and deficiencies associated with the cardiovascular system, urinogenital systems, biliary conduits, abdominal passageways and other biological vessels within the body. One embodiment of the system for treating vascular conditions, in accordance with the present invention, is illustrated in FIG. 1 at 100. Vascular condition treatment system 100 may include a catheter 110, a stent 120 coupled to the catheter, and a polymeric coating 122 on the stent or stent framework. Polymeric coating 122 may include a segmented chain copolyester. Polymeric coating 122 may include one or more bioactive agents dispersed throughout the coating. The bioactive agent may be a pharmacologically active drug or bioactive compound. The tailored polymeric coating may control the elution rate of the bioactive agent. Elution refers to the transfer of the bioactive agent out from polymeric coating 122. The elution is determined by the total amount of bioactive agent excreted from polymeric coating 122 into the body, typically measured in weight such as micrograms, or in weight per peripheral area of the stent. The polymeric coating including, for example, a segmented homochain copolyester, may be based on a predetermined elution rate of the bioactive drug. The polymeric coating may include between five and seventy-five percent of the bioactive drug by weight.

Upon insertion of catheter 110 and stent 120 with polymeric coating 122 into a directed vascular region of a human body, stent 120 may be expanded by applying pressure to a suitable balloon inside the stent, or by retracting a sheath to allow expansion of a self-expanding stent. Balloon deployment of stents and self-expanding stents are well known in the art. Catheter 110 may include the balloon used to expand stent 120. Catheter 110 may include a sheath that retracts to allow expansion of a self-expanding stent.

Another aspect of the present invention is a drug-polymer coated stent. The stent may include a stent framework. The drug-polymer coating may be included on the stent or stent framework. The polymeric coating may include a segmented homochain copolyester. A bioactive agent may be interdispersed within the polymeric coating. The drug polymer may contain one or more drugs or bioactive agents within the polymer or mixed with the polymer. The polymeric coating may include a primary coat and a cap coat, where the primary coat provides primarily a metal-adhering characteristic and the cap coat provides primarily a barrier membrane characteristic to control the elution of any bioactive agents in the primary coat or the cap coat.

Figure 2:
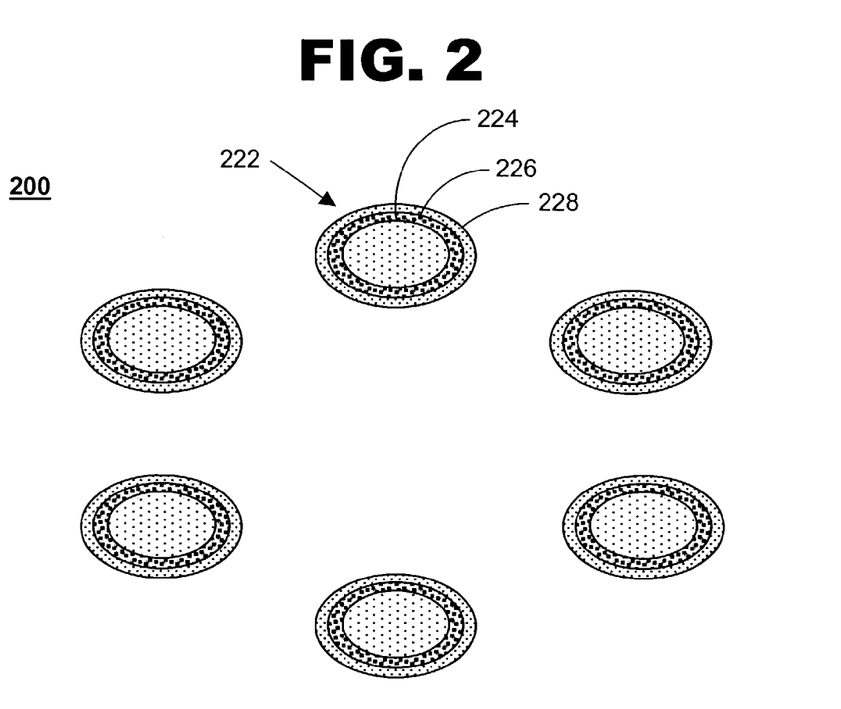
FIG. 2 is an illustration of a stent cross-section with a drug polymer coating the stent surface including a primary coat and a cap coat, in accordance with the current invention.

FIG. 2 shows an illustration of a stent cross-section containing a drug-polymer coating on the stent surface, in accordance with the present invention at 200. Drug-polymer coated stent 200 may include a polymeric coating 222 on a stent framework 224. Polymeric coating 222 may include a segmented homochain copolyester. Polymeric coating 222 may contain one or more pharmaceutical drugs or bioactive agents. Polymeric coating 222 may contain a polymeric matrix in which one or more bioactive agents are interdispersed.

The copolymer for coating the endovascular stent may include a number of hydrophobic sequences covalently linked to at least one hydrophilic sequence in the main chain, and a number of copolyester grafts including at least one hydrophobic sequence and at least one hydrophilic sequence covalently linked to the main chain. The hydrophobic sequence may include a butyl methacrylate derivative, and the hydrophilic sequence may include a vinyl acetate derivative.

The stent or stent framework 224 may include a base material of stainless steel, nitinol, tantalum or an MP35 N alloy. The stent or stent framework may include a base material of a suitable biocompatible alloy, or any other suitable biocompatible material including a polymeric material.

Drug-polymer coated stent 200 may include a single polymer coating on stent framework 224. Alternatively, polymer coating 222 may include a primary coat 226 on stent framework 224 and a cap coat 228 on the primary coat. Primary coat 226 may contain one or more pharmaceutical drugs or bioactive agents. Cap coat 228 may optionally include one or more interdispersed bioactive agents. The bioactive agents may be the same as those in the primary coat, or may be of different types and concentrations. Cap coat 228 and primary coat 226 may have similar constituents to allow physical interaction through common chain inter-diffusion between the two layers, improving the adhesion and minimizing the likelihood of delamination between the layers. The primary coat may have a predominantly hydrophilic characteristic to improve metal adhesion and, in some cases, to enhance the elution of embedded bioactive material. The cap coat may have a hydrophobic characteristic. A relatively hydrophobic characteristic may slow or mitigate the absorption of cap-coat polymeric material into the body, and in some cases, to provide a tailored barrier for the elution of bioactive material from the primary coat or the cap coat.

The bioactive agent may include an antisense agent, an antineoplastic agent, an antiproliferative agent, an antithrombogenic agent, an anticoagulant, an antiplatelet agent, an antibiotic, an anti-inflammatory agent, a gene therapy agent, a therapeutic substance, an organic drug, a pharmaceutical compound, a recombinant DNA product, a recombinant RNA product, a collagen, a collagenic derivative, a protein, a protein analog, a saccharide, or a saccharide derivative.

An antisense drug may work at the genetic level to interrupt the process by which disease-causing proteins are produced. An antineoplastic agent may prevent, kill, or block the growth and spread of cancer cells in the vicinity of the stent. An antiproliferative agent may prevent or stop cells from growing. An antithrombogenic agent may actively retard blood clot formation. An anticoagulant may delay or prevent blood coagulation with anticoagulant therapy, using compounds such as heparin and coumarins. An antiplatelet agent may act on blood platelets, inhibiting their function in blood coagulation. An antibiotic may kill or inhibit the growth of microorganisms and may be used to combat disease and infection. An anti-inflammatory agent may be used to counteract or reduce inflammation in the vicinity of the stent. A gene therapy agent may be capable of changing the expression of a person's genes to treat, cure or ultimately prevent disease. The bioactive agent may be any therapeutic substance that provides treatment of disease or disorders. An organic drug may be any small-molecule therapeutic material. A pharmaceutical compound may be any compound that provides a therapeutic effect. A recombinant DNA product or a recombinant RNA product may include altered DNA or RNA genetic material. Bioactive agents of pharmaceutical value may also include collagen and other proteins, saccharides, and their derivatives. The molecular weight of the bioactive agent may range from 200 to 60,000 Dalton and above.

The bioactive agent may be an agent against one or more conditions including coronary restenosis, cardiovascular restenosis, angiographic restenosis, arteriosclerosis, hyperplasia, and other diseases and conditions. For example, the bioactive agent may be selected to inhibit or prevent vascular restenosis, a condition corresponding to a narrowing or constriction of the diameter of the bodily lumen where the stent is placed. The bioactive agent may generally control cellular proliferation. The control of cell proliferation may include enhancing or inhibiting the growth of targeted cells or cell types.

Polymeric coating 122, 222 may elute at least one bioactive agent. Polymeric coating 122, 222 may include multiple bioactive agents. Polymeric coating 122, 222 may be tailored-to control the elution of one or more bioactive agents primarily by diffusion processes. In some cases, a portion of the polymeric coating may be absorbed by the body to release bioactive agents from within the coating.

Modification of the polymeric coatings may allow a bioactive agent with tailored elution properties to allow, for example, rapid delivery of the pharmacologically active drug within twenty-four hours of surgery, with a slower, steady delivery of a second bioactive agent, for example, over the next two to six months.

Figure 3:
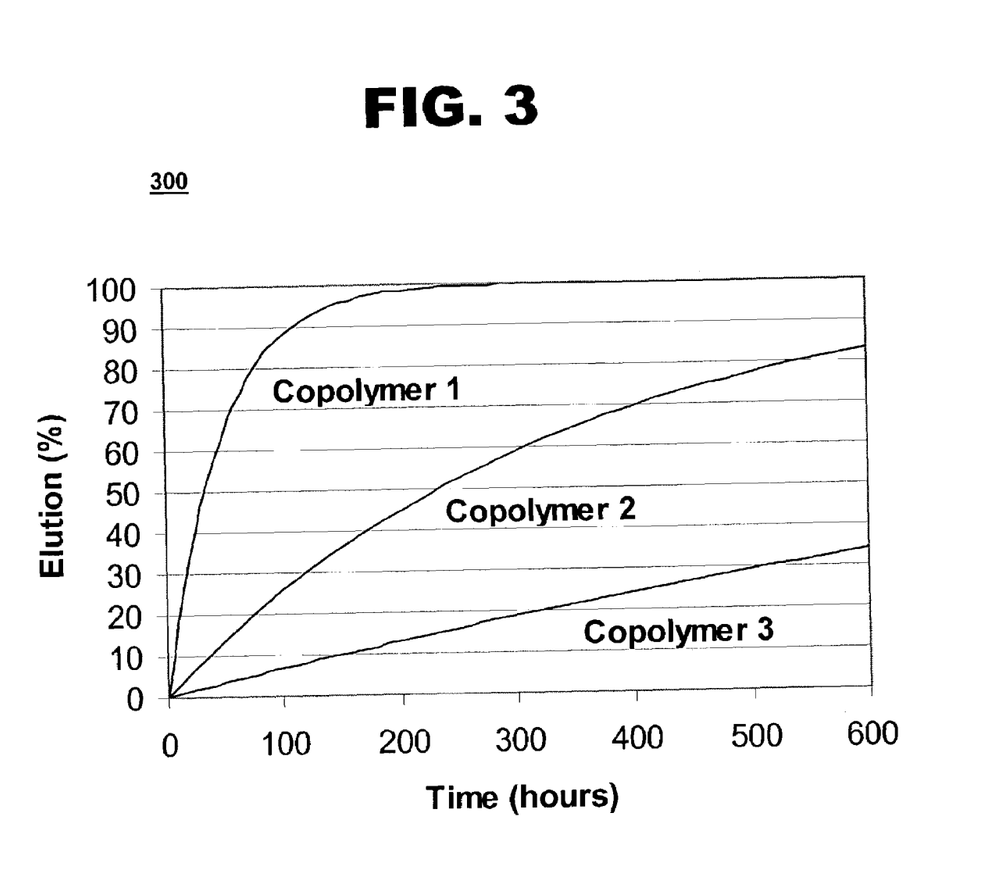
FIG. 3 is a graphical illustration of drug elution from a segmented homochain copolyester stent coating with an interdispersed bioactive agent, in accordance with the current invention.

FIG. 3 shows a graphical illustration of the elution of a bioactive agent from a drug-polymer coated stent, in accordance with the present invention at 300. Elution graph 300 shows the elution of a bioactive agent from a drug-polymer coated stent for three different profiles. The elution of the bioactive agent is indicated as a percentage of total drug dispersed within the stent coating. Typical units used for drug elution include micrograms of drug, or may be normalized to a unit volume with units such as micrograms per cubic centimeter of drug-polymer, or may be normalized to the periphery area of the stent with units such as micrograms per square centimeter. Elution profile of copolymer 1 of elution graph 300 shows a high rate of drug delivery over the initial period after stent deployment, whereas the elution profile of copolymer 2 and copolymer 3 of elution graph 300 shows a slower rate of drug delivery of a longer period of time, such as days, weeks or months. The elution profile of the bioactive agent may be established by the selection of the polymeric coating and the method of preparation. The elution rate may be determined from the elution graph by taking the derivative with respect to time, or by dividing the total amount of drug eluted by the elapsed time since stent deployment.

Another aspect of the present invention is a segmented homochain copolyester that may include hydrophobic methacrylate long sequences, or segments, linked at random to relatively more hydrophilic methacrylate-derived, or vinyl acetate-derived, segments (short sequences) or single sequences. The segmented homochain copolyester may include a number of segments of a first segment type linked to one or a number of segments of a second type, where the second segment type provides a metal-adhering characteristic, and the first segment type provides a hydrophobic barrier membrane characteristic. The weight fraction of the first segment type may be between five and ninety-five percent. A hydrophilic segment may provide better metal-adhering properties. A more hydrophobic segment may provide better membrane characteristics for slowing and controlling the elution rate of interdispersed drugs by serving as a membrane barrier.

A specific embodiment of this invention comprises a linear segmented copolyester with the following pairs of monomers wherein the second and first member of each pair may provide metal-adhering properties and hydrophobic barrier membrane properties, respectively. The second segment type may include vinyl acetate and/or vinyl alcohol and the first segment type may include n-butyl methacrylate. The second segment type may include vinyl acetate and the first segment type may include t-butyl methacrylate. The second segment type may include ethoxyethyl methacrylate and the first may include n-butyl methacrylate. The second segment type may include ethyl methacrylate and the first segment type may include n-butyl methacrylate. The second segment type may include methacrylic acid and the first segment type may include n-butyl methacrylate.

Another aspect of the present invention provides a segmented-grafted homochain copolyester comprising a random or segmented copolymeric main chain and a segmented graft, wherein the graft chain comprises sequences that may impart primarily hydrophobic barrier film properties while the main chain comprises sequences that may provide metal-adhering properties. In another embodiment, the role of the main chain and the graft may be reversed.

Figure 4:
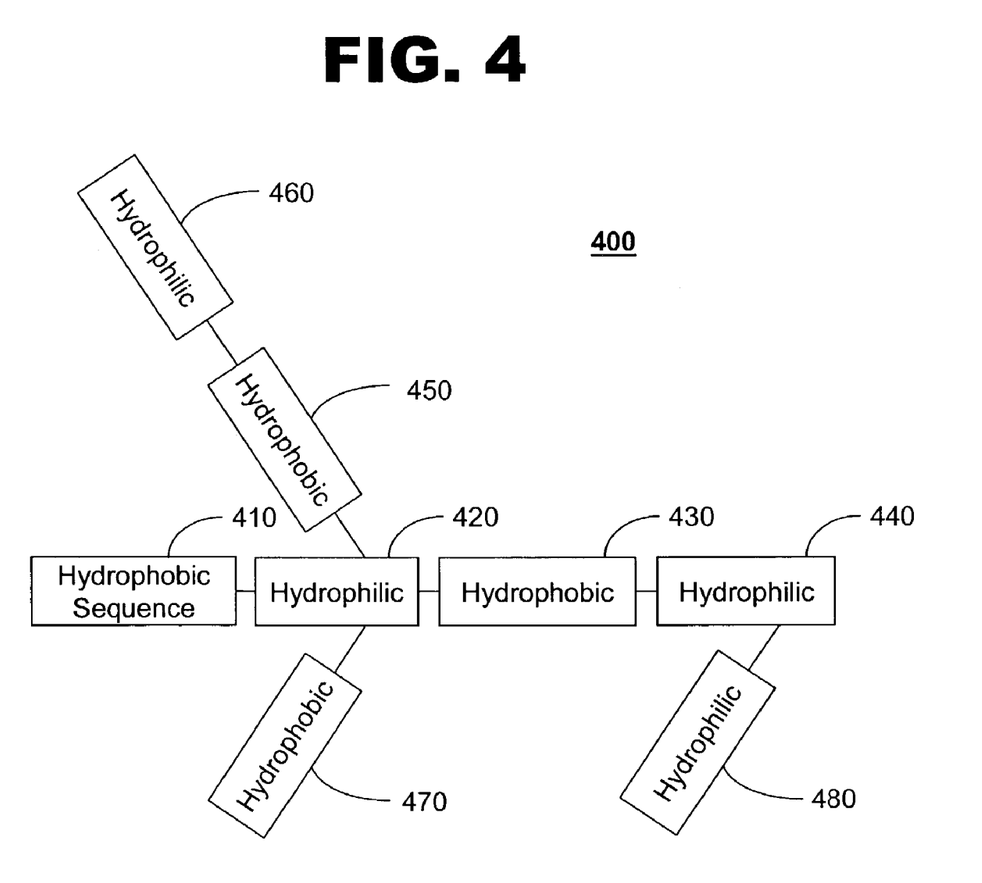
FIG. 4 is a schematic diagram of a segmented homochain copolyester with a plurality of polymer grafts, in accordance with the current invention.

FIG. 4 shows a schematic diagram of a segmented homochain copolyester with a plurality of polymer grafts, in accordance with the present invention at 400. Segmented-grafted homochain copolyester 400 may include a series of hydrophobic segments 410, 430 and hydrophilic segments 420, 440 connected in a main chain. Each hydrophobic and hydrophilic segment may include one or more repeat units. A plurality of segmented grafts comprising hydrophobic segments 450, 470 and hydrophilic segments 460, 480 may be attached to the segmented homochain copolyester. The grafts and segmented grafts may be pendant or attached to the hydrophilic segments in the main chain. Each of the segmented grafts may include at least one n-butyl methacrylate segment. Each of the segmented grafts may include at least one vinyl acetate and/or vinyl alcohol-based segment and at least one n-butyl methacrylate segment.

Segmented-grafted homochain copolyester 400 may comprise a copolymer main chain made primarily from vinyl acetate that is grafted with n-butyl methacrylate or grafted with segmented poly-n-butyl methacrylate sequences. In another embodiment, a random methacrylate copolymeric chain may be grafted with a mixture of vinyl acetate and a small fraction of n-butyl methacrylate.

All types of segmented homochain copolyesters (linear and graft type) described herein comprising vinyl acetate-derived sequences may have said sequences partially or fully hydrolyzed to produce the respective vinyl alcohol-based sequences. The latter are created to increase overall hydrophilicity of the copolyester and its propensity for hydrophilic bioactive agents.

Another aspect of the current invention is a method of manufacturing a drug-polymer stent. The drug-polymer stent may be manufactured by mixing a first monomer with a second monomer in a solution. The solution may include isopropyl alcohol. The mixture may be reacted to at least twenty percent conversion. Adding an aliquot of one of the second monomer or a mixture of the second monomer and the first monomer may further polymerize the mixture. A bioactive agent may be mixed with the polymerized mixture to form a drug polymer with a predefined elution rate. The drug polymer may be coated on a stent or stent framework. An incremental amount of free radical initiator may be added during the polymerization steps to initiate the polymer formation. The mixture may-be further polymerized by-adding additional stages of polymerization.

Figure 5:
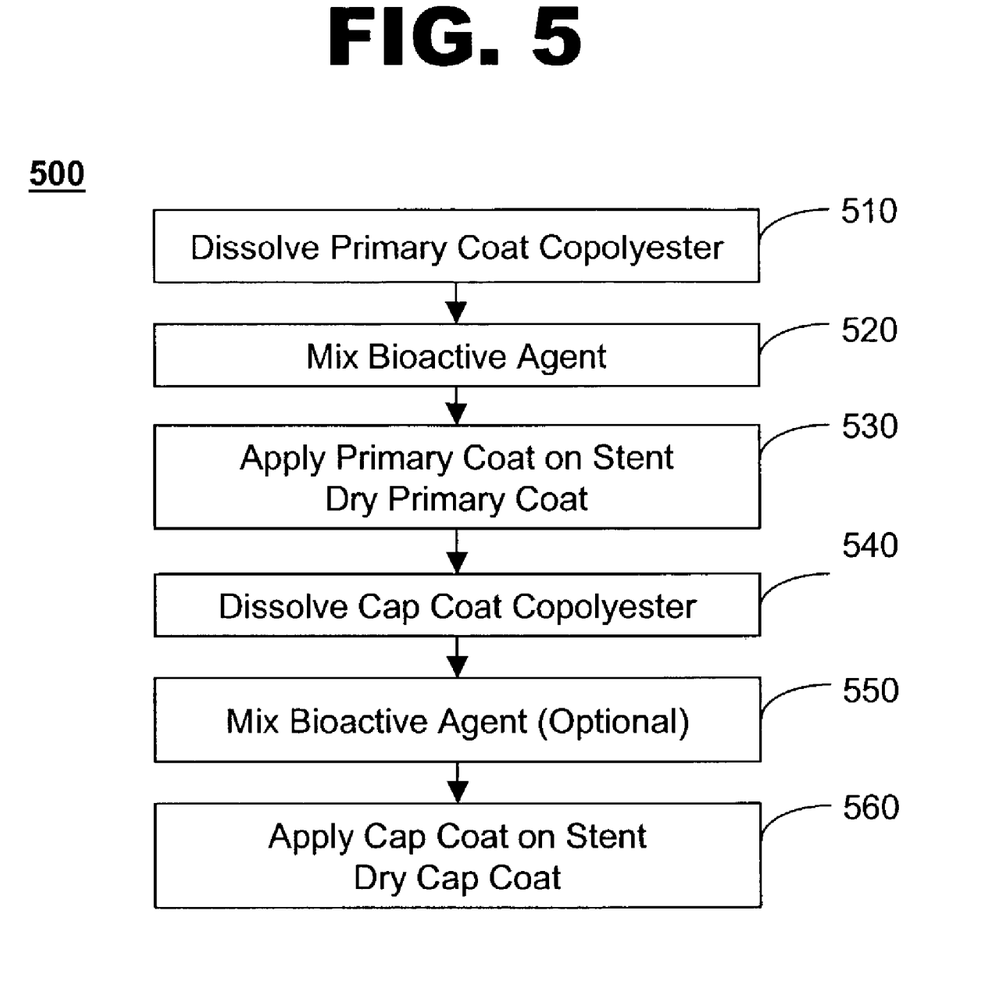
FIG. 5 is a flow diagram of one embodiment of a method for manufacturing a drug-polymer stent with a cap coat, in accordance with the current invention.

FIG. 5 shows a flow diagram of one embodiment of a method for manufacturing a drug-polymer stent including a cap coat, in accordance with the present invention at 500. A segmented homochain copolyester may be dissolved in a suitable primary coat liquid or solvent such as isopropyl alcohol, as seen at block 510. The primary coat may include a vinyl acetate derivative. A suitable bioactive agent or a solution containing the bioactive agent may be mixed in with the solution as seen at block 520, to provide between 1 percent and 70 percent bioactive agent by weight in the primary coat. The primary coat may be applied to a stent by dipping, spraying, painting, or any other suitable method for applying the polymer, and then dried as seen at block 530. Drying of the primary coat to eliminate or remove any volatile components may be done at room temperature or elevated temperatures under dry nitrogen or other suitable environment. The thickness of the primary coat may range between 0.05 millimeter and 0.2 millimeter, or greater.

A cap coat may be mixed in a suitable cap coat liquid or solvent, as seen at block 540. The cap coat may include a hydrophobic characteristic. The cap coat may include an n-butyl methacrylate derivative. A bioactive agent may optionally be added to the solution, as seen at block 550. The bioactive agent for the cap coat may be the same as the bioactive agent for the primary coat. A different bioactive agent may be used for the cap coat, and more than one bioactive agent may be used. The solution with or without a bioactive agent may be applied to the stent as a cap coat and dried, as seen at block 560. The solvent used with the cap coat may be selected such that the bioactive agent in the primary coat is not dissolved in the cap coat solvent. The cap coat solvent may be selected such that the primary coat liquid and the cap coat liquid are essentially immiscible. The bioactive agent in the cap coat may comprise between 0.01 percent and 30 percent of the cap coat by weight.

More specifically, illustrative examples of the present invention are provided herein.

EXAMPLE 1A

General Method of the Two-Step Synthesis of Segmented n-Butyl Methacrylate and Vinyl Acetate Copolymers One embodiment of the present invention is exhibited by a two-step synthesis of a copolymer with n-butyl methacrylate and vinyl acetate segments.

In the first step of the synthesis, predetermined amounts of n-butyl methacrylate (BMA) and vinyl acetate (VAc) were mixed in a pre-dried glass reactor equipped for mechanical stirring while providing a nitrogen environment about the reactants. The mixture was then sparged with nitrogen for about five minutes. A requisite amount of azo-bis-butyronitrile (Azo) was added to the mixture. In most cases, isopropyl alcohol (IPA) sparged with nitrogen was also added to the mixture. The mixture was heated to the desired temperature under nitrogen and stirred for a certain period of time until the commencement of the second step.

In the second step of the synthesis, a second aliquot of the Azo free radical initiator and IPA were added prior to introduction of a second charge of monomer or comonomer. The monomer and comonomer were also sparged with nitrogen. The polymerization was continued at the desired temperature until monomer consumption practically ceased, maintaining agitation while possible.

At the conclusion of the second step, the heating was stopped and the product was mixed in the reactor with a suitable solvent such as acetone to facilitate the polymer purification by precipitation in a cold non-solvent such as water or methanol or a mixture thereof. The precipitated copolymer was then isolated by filtration and allowed to dry in a laminar flow hood under reduced pressure at room temperature until a constant dry weight was achieved. Further drying can be accomplished by heating under reduced pressure until a constant dry weight is achieved.

EXAMPLE 1B

General Methods of Analysis

A set of general analysis methods was used to monitor and characterize the polymerization reactions. In-process monitoring of the polymerization reaction was achieved by the analysis of residual monomers and molecular weight build-up using gel permeation chromatography (GPC) with dichloromethane as a solvent.

The purified copolymer was characterized With infrared analysis using a film prepared from a chloroform solution. The composition of the purified copolymer was determined with nuclear magnetic resonance (NMR), using $CDCL_3$ as a solvent. Weight average molecular weight (Mw) was measured using GPC with dichloromethane (DCM) or tetrahydrofuran (THF) as a solvent, and the inherent viscosity (I.V.) with chloroform.

EXAMPLE 1C

General Method of Film Formation and Determination of Percent Elongation

Fracture strain characteristics of the polymeric material may be measured by forming the polymer into a sheet, and applying strain to a sample of the material, and determining when the sample breaks, thereby determining the fracture strain.

The dried polymer was compression-molded into a film about 0.1 mm thick using a heated laboratory Carver press. The temperature, pressure, and time used varied with the copolymer composition—typically above 50° C., 3,000 lbs, and 2 minutes, respectively. The pressed polymer was then quick-quenched to about 25° C. and removed. The molded film was cut into 13×40 mm pieces. The percent elongation was determined on a Mini-Bionix Universal Tester using a gauge length of 19 mm and strain rate of 0.5 mm/s.

EXAMPLES 2A–2J

Two-Step Synthesis of VAc and BMA Segmented Chain Copolymer with BMA in the Second Step A segmented chain copolymer was synthesized in a two-step procedure using only BMA in the second step. Reaction charge and conditions for the preparation of ten copolymers are summarized in Table IA and Table 1B. The copolymers were made using a (1) high VAc to BMA ratio and only BMA in the second step; (2) polymerization temperature of 55° C. to 70° C.; and (3) no or variable amounts of IPA.

TABLE 1A

Two-step Synthesis and Properties of Segmented VAc to BMA Copolymers Using only BMA in the Second Step

| Example Number | 2A | 2B | 2C | 2D | 2E |
|---|---|---|---|---|---|
| Step 1 | | | | | |
| VAc/BMA (g/g) | 8/2 | 23/6 | 94/100 | 90/10 | 80/20 |
| Azo (mg) | 38 | 100 | 249 | 249 | 300 |
| IPA (ml) | 0 | 0 | 100 | 10 | 10 |
| R Time (hour)/Temp (° C.) | 1/70 | 1/70 | 20/60 | 23/60 | 53/55 |
| Step 2 | | | | | |
| BMA/VAc (g/g) | 8/0 | 22/0 | 100/0 | 100/0 | 100/0 |
| Azo (mg) | 0 | 0 | 101 | 101 | 80 |
| IPA (ml) | 0 | 0 | 100 | 100 | 100 |
| R Time (hour)/Temp (° C.) | 35/70 | 35/70 | 26/60 | 21/60 | 37/60 |
| Polymer Properties I.V. | 1.04 | 1.44 | 0.6 | 1.24 | 0.75 |
| $M_w$ (kDa)[1] | >377[2] | 258 | 163 | 395 | 222 |
| Elongation (%) | >250 | >250 | >250 | >250 | >250 |

[1]In DCM or otherwise as indicated.
[2]In THF.

TABLE 1B

Two-step Synthesis and Properties oT Segmented VAc and BMA Copolymers Using only BMA in the Second Step

| Example Number | 2F | 2G | 2H | 2I | 2J |
|---|---|---|---|---|---|
| Step 1 | | | | | |
| VAc/BMA (g/g) | 25/8 | 20/8 | 18/10 | 70/10 | 70/10 |
| Azo (mg) | 105 | 100 | 105 | 250 | 250 |
| IPA (ml) | 0 | 0 | 0 | 10 | 10 |
| R Time (hour)/Temp (° C.) | 1/70 | 1/70 | 1/70 | 54/60 | 46/60 |
| Step 2 | | | | | |
| BMA/VAc (g/g) | 22/0 | 20/0 | 22/0 | 120/0 | 120/0 |
| Azo (mg) | 0 | 0 | 0 | 80 | 80 |
| IPA (ml) | 0 | 0 | 0 | 12 | 20 |
| R Time (hour)/Temp (° C.) | 35/70 | 35/70 | 35/70 | 30/60 | 23/60 |
| Polymer Properties I.V. | 1.66 | 1.39 | 1.63 | 0.81 | 0.74 |

TABLE 1B-continued

Two-step Synthesis and Properties oT Segmented VAc and BMA Copolymers Using only BMA in the Second Step

| Example Number | 2F | 2G | 2H | 2I | 2J |
|---|---|---|---|---|---|
| $M_w$ (kDa)[1] | 273 | 268 | 275 | 225 | 264 |
| Elongation (%) | >250 | >250 | >250 | >250 | >250 |

[1]In DCM.

EXAMPLES 3A AND 3B

Two-Step Synthesis of Segmented Polymers of Ethyl Methacrylate with Two Other Comonomers A segmented copolymer was synthesized in a two-step process using ethyl methacrylate (EMA) and two other comonomers. Reaction charge and conditions for the bulk preparation (no IPA was used) of a segmented copolymer of EMA with VAc and BMA are summarized in Table II for Example 3A. No IPA was used in the preparation. Example 3B is also described in Table II. It is based on EMA, ethoxyethyl methacrylate (ETOEMA) and BMA. The properties of the polymers in Examples 3A and 3B are also outlined in Table II.

TABLE II

Two-Step Synthesis and Properties of Segmented Polymers of Ethyl Methacrylate (EMA) with Two Other Comonomers

| Example Number | 3A | 3B |
|---|---|---|
| Step 1 | 20/15 | 20/7.5 |
| Added Monomers (g) | VAc/EMA | ETOEMA/EMA |
| Azo (mg) | 100 | 100 |
| R Time (hour)/Temp (° C.) | 2.5/70 | 0.7/70 |
| Step 2 | 7.5 | 22.5 |
| Added Monomer (g) | BMA | BMA |
| R Time (hour)/Temp (° C.) | 34/70 | 2/70 |
| Polymer Properties I.V. | 1.84 | 1.57 |
| $M_w$ (kDa)* | — | — |
| Elongation (%) | >250 | >250 |

*In DCM.

EXAMPLES 4A–4E

Synthesis of Segmented BMA and VAc Copolymers with at Least 90:10 MBA to. VAc Comonomer Ratio A segmented BMA-VAc copolymer with a MBA to VAc comonomer ratio of at least 90:10 was synthesized. A two-step synthetic scheme was used to prepare the copolymer of Example 4A and entailed 1) a brief first step of one copolymerization cycle associated with incomplete consumption of the comonomer; and 2) the addition of a second aliquot of Azo initiator at the beginning of the second copolymerization step. In Example 4B, the copolymerization was conducted in an extended single step using a high single dose of the Azo initiator. The synthesis of Examples 4C and 4D polymers entailed preparing a low molecular prepolymer of one type in the first step and adding a monomer mixture that was rich in BMA in the second step.

In Example 4E, a slightly higher temperature was used in the second step. Reaction charges for the preparation of the copolymers of Examples 4A to 4E and their properties are summarized in Table III.

TABLE III

Synthesis and Properties of BMA and VAc Segmented Copolymers With at Least 90:10 BMA:VAc Comonomer Ratio

| Example Number | 4A | 4B | 4C | 4D | 4E |
|---|---|---|---|---|---|
| Step 1 | | | | | |
| VAG/BMA (g/g) | 10.5/200 | 20/180 | 15/0 | 0/195 | 15/0 |
| Azo (mg) | 250 | 300 | 200 | 200 | 200 |
| IPA (ml) | 100 | 100 | 100 | 150 | 100 |
| R Time (hr)/Temp (° C.) | 10/65 | 21/65 | 16/65 | 12/65 | 16/65 |
| Step 2 | | | | | |
| BMA/VAc (g/g) | 0/0 | 0/0 | 5/180 | 10.5/5 | 5/180 |
| Azo (mg) | 50 | 50 | 150 | 200 | 150 |
| R Time (hr)/Temp (° C.) | 7/65 | 7/65 | 12/65 | 16/65 | 12/70 |
| Polymer Properties I.V. | 1.08 | — | — | — | — |
| $M_w$ (kDa)* | 314 | 183 | 260 | 300 | 310 |
| Elongation (%) | >250 | >250 | >250 | >250 | >250 |

*In DCM.

EXAMPLES 5A–5D

Synthesis of Segmented VAc and BMA Copolymers with at Least 90:10 VAc:BMA Comonomer Ratio A segmented VAc and BMA copolymer with greater than 90:10 VAc to BMA comonomer ratio was synthesized in a two-step process. The two-step synthesis schemes outlined in Table IV were used to prepare the copolymers of Examples 5A and 5B. These entailed 1) charging all reactants at the first step; 2) using a relatively higher Azo concentration than those used in the previous examples; 3) extending the reaction time in the first step; and 4) limiting the reaction temperature in the second step to 25° C. For the copolymers of Examples 5C and 5D as in Table IV, the BMA was charged at both steps and an additional amount of IPA was used in the second step.

TABLE IV

Synthesis and Properties of VAc and BMA Segmented Copolymers With at Least 90:10 VAc:BMA Comonomer Ratio

| Example | 5A | 5B | 5C | 5D |
|---|---|---|---|---|
| Step 1 | | | | |
| VAc/BMA (g/g) | 190/10 | 180/20 | 180/10 | 180/15 |
| Azo (mg) | 300 | 300 | 300 | 300 |
| IPA (ml) | 100 | 100 | 100 | 100 |
| R time (hour)/Temp (° C.) | 30/65 | 30/65 | 30/65 | 30/65 |
| Step 2 | | | | |
| BMA/VAc (g/g) | 0/0 | 0/0 | 0/10 | 0/5 |
| Azo (mg) | 0 | 0 | 0 | 0 |
| IPA (ml) | 0 | 0 | 100 | 100 |
| R time (hour)/Temp (° C.) | 12/25 | 12/25 | 12/65 | 12/65 |
| Polymer Properties I.V. | — | 0.25 | — | — |
| $M_w$ (kDa)* | — | 59 | — | — |
| Elongation (%) | >250 | >250 | >250 | >250 |

*In DCM.

EXAMPLE 6

Synthesis of Segmented VAc and BMA Copolymer with 50:50 VAc:BMA Comonomer Ratio A segmented VAc and BMA copolymer with approximately 50:50 VAc:BMA comonomer ratio by weight was synthesized in a multi-step process. The multi-step synthetic scheme was used to prepare the 50:50 copolymer following the general experimental protocol as described in Example 1 for VAc and BMA copolymerization with the Azo initiator and IPA as a diluent and reaction medium. In the first step, 85 g of VAc was allowed to copolymerize with 10 g of BMA using 200 mg of the Azo initiator and 75 ml of IPA. The polymerization was conducted at 65° C. for 24 hours. At the conclusion of the first step, a mixture of 5 g VAc, 30 g BMA, 50 mg Azo, and 25 ml IPA was added to the reaction product to proceed with the second step. At this step, the copolymerization was conducted at a temperature at about 65° C. for 6 hours. A similar charge was used in the third step, and the copolymerization was conducted at 65° C. for 16 hours. In the fourth step, the same comonomer, Azo and IPA charge was used, and the copolymerization was conducted at 65° C. for 16 hours. At the conclusion of the fourth step, the copolymer may be isolated, purified, and characterized in the manner as described in Example 1.

EXAMPLE 7

Synthesis of Segmented Interpenetrating VAc and BMA Copolymer with an Overall Comonomer Ratio of 50:50

A segmented copolymer consisting of interpenetrating VAc and BMA sequences with an average comonomer ratio of 50:50 by weight was synthesized. The polymerization was conducted in two steps under the general experimental conditions noted in earlier examples. In the first step, a mixture of 90 g VAc, 10 g BMA, 350 mg Azo, and 100 ml IPA was heated at 65° C. for 24 hours. At the conclusion of the first step, a mixture of 10 g VAc, 90 g MBA and 50 ml IPA was added to the reaction mixture, and heated to 65° C. and held there for 16 hours during the second step. The resulting polymer may be isolated, purified, and characterized as described in previous examples.

EXAMPLE 8

Synthesis of Segmented Terpolymer of VAc, BMA, and a Small Fraction of Methacrylic Acid with a Comonomer Ratio of 2:8:90 MMA:VAC:BMA In another embodiment of the present invention, a small fraction of methacrylic acid (MAA) was combined with VAc and BMA to form a segmented terpolymer with a comonomer ration of 2:8:90 MMA:VAc:BMA. The polymerization was conducted in two steps under the general experimental conditions reported in earlier examples. In the first step, a mixture of 1 g methacrylic acid, 6 g VAc, 50 g BMA, 200 mg Azo, and 75 ml IPA was heated for 21 hours at 65° C. At the conclusion of the first step, a mixture of 1 g MAA, 2 g VAc, 40 g BMA, 100 mg Azo, and 75 ml IPA was added to conduct the second step for 12 hours at 65° C. The resulting polymer may be isolated, purified, and characterized as described earlier.

EXAMPLE 9

Synthesis of Segmented 94:5 VAc:BMA Copolymer Grafted with Short 1:20 VAc:BMA Chains, for an Overall Comonomer Ratio of 95:25 VAc:BMA A segmented copolymer consisting of a 94:5 VAc:BMA copolymer grafted with short 1:20 VAc:BMA chains was synthesized in accordance with another embodiment of the present invention, to form a grafted copolymer with an overall comonomer ratio of 95:25. The polymerization was conducted in two steps, under the usual experimental conditions noted in earlier examples. In the first step, a mixture of 94 g VAc, 5 g BMA, 250 mg Azo, and 100 ml IPA was heated at 65° C. for 24 hours. At the conclusion of this period, 100 ml of IPA were added to the reaction product. This was followed by adding 50 mg of Azo and continuing the heating at 65° C. for 5 minutes prior to adding a mixture of 1 g VAc and 20 g BMA, and then proceeding with the second step of the copolymerization at 65° C. for 12 hours. The resulting polymer may be isolated, purified, and characterized as described in previous examples.

EXAMPLE 10

Preparation of Poly(n-Butyl Methacrylate)

In another embodiment of the current invention, a segmented copolymer was prepared with poly(n-butyl methacrylate). This entailed the use of 200 g BMA, 408 mg Azo initiator, and 150 ml IPA. The polymerization was conducted at 65° C. for 18 hours. The resulting polymer was isolated, purified, and characterized in the usual manner (see Example 1). The polymer was shown to have an I.V. of 0.82 dL/g, $M_w$, (DCM) of 263 kiloDalton (kDa), and its film did not break at over 300% elongation.

EXAMPLE 11

Stent Coating with Example 5B Polymers as the Primary Coat and Example 10 Polymers as the Cap Coat, with a Bioactive Drug at 30 Percent Loading A stent coating with a primary coat using segmented polymers as in Example 5B and with an outer or cap coat using segmented polymers as in Example 10 was formed with a bioactive drug of 30 percent by weight, in accordance with another embodiment of the present invention.

A copolymer as defined in Example B was mixed in an organic solvent such as tetrahydrofuran (THF), chloroform or a similar organic solvent with 30% by weight of drug was added to the Example 5B polymer solution to 1% total solids. The solution was filtered using a 0.2–0.5 micron filter and applied to the stent using a commercially available spray apparatus. The coated stent was dried to remove volatile solvents prior to experimental use.

EXAMPLE 12

Stent Coating with Example 5B Polymers as the Primary Coat and Example 10 Polymers as the Cap Coat, with a Bioactive Drug at 20 Percent Loading A stent coating with a primary coat using segmented polymers as in Example 5B and with an outer or cap coat using segmented polymers as in Example 10 was formed with a bioactive drug of 20 percent by weight, in accordance with another embodiment of the present invention.

A copolymer as defined in Example B was mixed in an organic solvent such as tetrahydrofuran (THF), chloroform or a similar organic solvent with 30% by weight of drug was added to the Example 5B polymer solution to 1% total solids. The solution was filtered using a 0.2–0.5 micron filter and applied to the stent using a commercially available spray apparatus. The coated stent was dried to remove volatile solvents prior to experimental use.

EXAMPLE 13

In Vitro Release Experiment with Coated Stents

An in vitro release experiment with segmented copolymer coated stents as in Example 11 and Example 12 was completed. Drug-polymer coated stents were placed in PBS at 37 degrees centigrade. Samples were shaken at about 80 cycles per minute. Aliquots of PBS were tested using high performance liquid chromatography (HPLC) to determine the amount of drug eluted. Results may be reported in the form of percent drug per time interval or amount of drug or weight of drug per time interval.

EXAMPLE 14

Assembling a System Comprising a Catheter Coupled with a Coated Stent

A system for treating vascular conditions such as heart disease was assembled using a catheter and a stent coupled to the catheter. The stent was coated with a segmented homochain copolyester with an interdispersed bioactive agent. Finished coated stents, such as described in Example 11, may be reduced in diameter and placed into the distal end of the catheter, in a fashion to form an interference fit that secures the stent onto the catheter. The catheter with the stent may be placed in a catheter package and sterilized prior to shipping and storing. Sterilization using conventional means may be accomplished before clinical use.

While the embodiments of the invention disclosed herein are presently considered to be preferred, various changes and modifications can be made without departing from the spirit and scope of the invention. The scope of the invention is indicated in the appended claims, and all changes that come within the meaning and range of equivalents are intended to be embraced therein.

The invention claimed is:

1. A system for treating a vascular condition, comprising:
a catheter;
a stent coupled to the catheter;
a polymeric coating on the stent, wherein the polymeric coating comprises a segmented homochain copolyester having a plurality of segments of a first segment type comprising methacrylate sequences randomly linked to one or a plurality of segments of a second segment type comprising vinyl acetate sequences wherein said first segment type is selected from the group consisting of t-butyl methacrylate and n-butyl methacrylate and said second segment type is selected from the group consisting of vinyl acetate, ethoxyethyl methacrylate, ethyl methacrylate and methacrylic acid wherein the second segment type comprises vinyl acetate and the first segment type comprises n-butyl methacrylate, the second segment type comprises vinyl acetate and the first segment type comprises t-butyl methacrylate, the second segment type comprises ethoxyethyl methacrylate and the first segment type comprises n-butyl methacrylate, the second segment type comprises ethyl methacrylate and the first segment type comprises n-butyl methacrylate, and the second segment type comprises methacrylic acid and the first segment type comprises n-butyl methacrylate; and
a bioactive drug dispersed within the polymeric coating.

2. The system of claim 1 wherein the plurality of segments of a first segment type provide a hydrophobic barrier membrane characteristic and the plurality of segments of a second segment type provide a metal-adhering characteristic.

3. The system of claim 1 where-in the segmented homochain copolyester comprises between 5 percent and 95 percent by weight of the first segment type.

4. The system of claim 1 wherein the second segment type comprises vinyl acetate and the first segment type comprises n-butyl methacrylate.

5. The system of claim 1 wherein the second segment type comprises vinyl acetate and the first segment type comprises t-butyl methacrylate.

6. The system of claim 1 wherein the second segment type comprises ethoxyethyl methacrylate and the first segment type comprises n-butyl methacrylate.

7. The system of claim 1 wherein the second segment type comprises ethyl methacrylate and the first segment type comprises n-butyl methacrylate.

8. The system of claim 1 wherein the second segment type comprises methacrylic acid and the first segment type comprises n-butyl methacrylate.

9. The system of claim 1 further comprising:
a plurality of segmented grafts attached to the segmented homochain copolyester.

10. The system of claim 9 wherein each of the segmented grafts comprise at least one n-butyl methacrylate segment.

11. The system of claim 10 wherein each of the segmented grafts comprise at least one vinyl acetate segment and at least one n-butyl methacrylate segment.

12. The system of claim 1 wherein the segmented homochain copolyester is based on a predetermined elution rate of the bioactive drug.

13. The system of claim 1 wherein the polymeric coating comprises between 5 percent and 75 percent by weight of the bioactive drug.

14. The system of claim 1 wherein the bioactive drug is selected from a group consisting of an antisense agent, an antineoplastic agent, an antiproliferative agent, an anti-thrombogenic agent, an anticoagulant, an antiplatelet agent, an antibiotic and an anti-inflammatory agent.

15. The system of claim 1 wherein the bioactive agent controls cellular proliferation.

16. The system of claim 1 wherein the polymeric coating on the stent comprises a primary coat and a cap coat on the primary coat.

17. The system of claim 16 wherein the primary coat comprises a bioactive agent between 1 and 70 percent by weight interdispersed within the primary coat.

18. The system of claim 16 wherein the cap coat includes a hydrophobic characteristic.

19. The system of claim 16 wherein the primary coat comprises a vinyl acetate derivative, and the cap coat comprises an n-butyl methacrylate derivative.

20. The system of claim 16 wherein the cap coat comprises a second bioactive agent between 0.01 percent and 30 percent by weight interdispersed within the cap coat.

21. The system of claim 1 wherein the polymeric coating on the stent comprises a fracture strain characteristic of greater than 200 percent.

22. The system of claim 1 wherein the catheter includes a balloon used to expand the stent.

23. The system of claim 1 wherein the catheter includes a sheath that retracts to allow expansion of the stent.

24. The system of claim 1 wherein the stent comprises a base metal selected from a group consisting of stainless steel, nitinol, tantalum, MP35N alloy, a suitable biocompatible alloy, and a suitable biocompatible material.

* * * * *